(12) United States Patent
Herweck et al.

(10) Patent No.: US 8,021,331 B2
(45) Date of Patent: Sep. 20, 2011

(54) METHOD OF COATING A FOLDED MEDICAL DEVICE

(75) Inventors: Steve A. Herweck, Nashua, NH (US); Paul Martakos, Pelham, NH (US); Geoffrey Moodie, Hudson, NH (US); Roger Labrecque, Londonderry, NH (US); Theodore Karwoski, Hollis, NH (US); Trevor Carlton, Hudson, NH (US); Lisa Rogers, Londonderry, NH (US); Joseph Ferraro, Londonderry, NH (US)

(73) Assignee: Atrium Medical Corporation, Hudson, NH (US)

( * ) Notice: Subject to any disclaimer, the term of this patent is extended or adjusted under 35 U.S.C. 154(b) by 567 days.

(21) Appl. No.: 11/250,768

(22) Filed: Oct. 14, 2005

(65) Prior Publication Data

US 2006/0112536 A1    Jun. 1, 2006

Related U.S. Application Data

(63) Continuation-in-part of application No. 10/943,075, filed on Sep. 15, 2004, now abandoned.

(60) Provisional application No. 60/503,357, filed on Sep. 15, 2003.

(51) Int. Cl.
*A61M 37/00* (2006.01)
*A61M 31/00* (2006.01)

(52) U.S. Cl. ............... 604/103.08; 604/103.02

(58) Field of Classification Search ............ 604/103.02, 604/103.06–103.08
See application file for complete search history.

(56) References Cited

U.S. PATENT DOCUMENTS

| | | | |
|---|---|---|---|
| 4,824,436 | A | 4/1989 | Wolinsky |
| 4,941,877 | A | 7/1990 | Montano, Jr. |
| 4,994,033 | A | 2/1991 | Shockey et al. |
| 5,041,125 | A | 8/1991 | Montano, Jr. |
| 5,087,244 | A | 2/1992 | Wolinsky et al. |
| 5,087,246 | A * | 2/1992 | Smith ............... 604/103.13 |

(Continued)

FOREIGN PATENT DOCUMENTS

DE    10115740 A1    10/2002

(Continued)

OTHER PUBLICATIONS

A paper entitled, "Evaluation of the Biocompatibility and Drug Delivery Capabilities of Biological Oil Based Stent Coatings," by Li, Shengqiao of the Katholieke Universiteit Leuven.

(Continued)

*Primary Examiner* — Nicholas D Lucchesi
*Assistant Examiner* — Victoria P Campbell
(74) *Attorney, Agent, or Firm* — Morse, Barnes-Brown & Pendelton, P.C.; Sean D. Detweiler, Esq.

(57) ABSTRACT

A non-polymeric or biological coating applied to a radially expandable interventional medical device in a collapsed, wrapped, or folded configuration. Properties of the coating material applied to the medical device are adjusted or varied to result in a desired combination of coverage of the surface of the medical device, drug loading, and coating thickness. The coating is sterile, and is capable of being carried by a sterile medical device to a targeted tissue location within the body following radial expansion. The therapeutic coating transfers off the medical device due in part to a biological attraction with the tissue and in part to a physical transference from the medical device to the targeted tissue location in contact with the medical device.

14 Claims, 5 Drawing Sheets

U.S. PATENT DOCUMENTS

| | | | |
|---|---|---|---|
| 5,102,402 A | 4/1992 | Dror et al. | |
| 5,199,951 A | 4/1993 | Spears | |
| 5,267,985 A | 12/1993 | Shimada et al. | |
| 5,279,565 A | 1/1994 | Klein et al. | |
| 5,282,785 A | 2/1994 | Shapland et al. | |
| 5,286,254 A | 2/1994 | Shapland et al. | |
| 5,295,962 A | 3/1994 | Crocker et al. | |
| 5,304,121 A | 4/1994 | Sahatjian | |
| 5,336,178 A | 8/1994 | Kaplan et al. | |
| 5,447,940 A | 9/1995 | Harvey et al. | |
| 5,456,666 A | 10/1995 | Campbell et al. | |
| 5,458,568 A | 10/1995 | Racchini et al. | |
| 5,458,572 A * | 10/1995 | Campbell et al. | 604/103.08 |
| 5,498,238 A | 3/1996 | Shapland et al. | |
| 5,499,971 A | 3/1996 | Shapland et al. | |
| 5,509,899 A | 4/1996 | Fan et al. | |
| 5,514,092 A | 5/1996 | Forman et al. | |
| 5,569,198 A | 10/1996 | Racchini | |
| 5,628,730 A | 5/1997 | Shapland et al. | |
| 5,634,899 A | 6/1997 | Shapland et al. | |
| 5,637,113 A | 6/1997 | Tartaglia et al. | |
| 5,693,014 A * | 12/1997 | Abele et al. | 604/103.08 |
| 5,700,286 A | 12/1997 | Tartaglia et al. | |
| 5,749,845 A | 5/1998 | Hildebrand et al. | |
| 5,800,392 A | 9/1998 | Racchini | |
| 5,807,306 A | 9/1998 | Shapland et al. | |
| 5,865,787 A | 2/1999 | Shapland et al. | |
| 5,902,266 A | 5/1999 | Leone et al. | |
| 6,010,480 A * | 1/2000 | Abele et al. | 604/103.06 |
| 6,013,055 A * | 1/2000 | Bampos et al. | 604/103.07 |
| 6,015,844 A | 1/2000 | Harvey et al. | |
| 6,033,380 A * | 3/2000 | Butaric et al. | 604/103.07 |
| 6,048,332 A | 4/2000 | Duffy et al. | |
| 6,120,477 A | 9/2000 | Campbell et al. | |
| 6,120,789 A * | 9/2000 | Dunn | 424/426 |
| 6,146,358 A | 11/2000 | Rowe | |
| 6,200,985 B1 | 3/2001 | Cottens et al. | |
| 6,206,916 B1 | 3/2001 | Furst | |
| 6,231,600 B1 | 5/2001 | Zhong | |
| 6,287,285 B1 | 9/2001 | Michal et al. | |
| 6,299,604 B1 | 10/2001 | Ragheb et al. | |
| 6,355,063 B1 | 3/2002 | Calcote | |
| 6,358,556 B1 | 3/2002 | Ding et al. | |
| 6,364,856 B1 | 4/2002 | Ding et al. | |
| 6,364,893 B1 | 4/2002 | Sahatjian et al. | |
| 6,364,903 B2 | 4/2002 | Tseng et al. | |
| 6,369,039 B1 | 4/2002 | Palasis et al. | |
| 6,451,373 B1 | 9/2002 | Hossainy et al. | |
| 6,491,938 B2 | 12/2002 | Kunz | |
| 6,500,174 B1 | 12/2002 | Maguire | |
| 6,534,693 B2 | 3/2003 | Fischell et al. | |
| 6,541,116 B2 | 4/2003 | Michal et al. | |
| 6,544,223 B1 | 4/2003 | Kokish | |
| 6,544,224 B1 * | 4/2003 | Steese-Bradley | 604/103.06 |
| 6,610,035 B2 | 8/2003 | Yang et al. | |
| 6,616,650 B1 | 9/2003 | Rowe | |
| 6,641,611 B2 | 11/2003 | Jayaraman | |
| 6,730,064 B2 | 5/2004 | Ragheb et al. | |
| 6,758,847 B2 | 7/2004 | Maguire | |
| 6,764,509 B2 | 7/2004 | Chinn et al. | |
| 6,808,536 B2 | 10/2004 | Wright et al. | |
| 6,833,004 B2 | 12/2004 | Ishii et al. | |
| 6,899,729 B1 | 5/2005 | Cox et al. | |
| 6,918,927 B2 | 7/2005 | Bates et al. | |
| 7,090,655 B2 | 8/2006 | Barry | |
| 2002/0082679 A1 | 6/2002 | Sirhan et al. | |
| 2002/0183716 A1 | 12/2002 | Herweck et al. | |
| 2003/0083740 A1 | 5/2003 | Pathak | |
| 2003/0152609 A1 | 8/2003 | Fischell et al. | |
| 2003/0204168 A1 | 10/2003 | Bosma et al. | |
| 2004/0006296 A1 | 1/2004 | Fischell et al. | |
| 2004/0018228 A1 | 1/2004 | Fischell et al. | |
| 2004/0039441 A1 | 2/2004 | Rowland et al. | |
| 2004/0071756 A1 | 4/2004 | Fischell et al. | |
| 2004/0073284 A1 | 4/2004 | Bates et al. | |
| 2004/0102758 A1 | 5/2004 | Davila et al. | |
| 2004/0137066 A1 | 7/2004 | Jayaraman | |
| 2004/0167572 A1 | 8/2004 | Roth et al. | |
| 2004/0230176 A1 | 11/2004 | Shanahan et al. | |
| 2004/0235762 A1 | 11/2004 | Abel et al. | |
| 2005/0084514 A1 | 4/2005 | Shebuski et al. | |
| 2005/0101522 A1 | 5/2005 | Speck et al. | |
| 2005/0113687 A1 | 5/2005 | Herweck et al. | |
| 2005/0158361 A1 | 7/2005 | Dhondt et al. | |
| 2005/0159809 A1 | 7/2005 | Hezi-Yamit et al. | |
| 2005/0182485 A1 | 8/2005 | Falotico et al. | |
| 2005/0187376 A1 | 8/2005 | Pacetti | |
| 2005/0232971 A1 | 10/2005 | Hossainy et al. | |
| 2006/0008501 A1 | 1/2006 | Dhont et al. | |
| 2006/0036311 A1 | 2/2006 | Nakayama et al. | |
| 2006/0067974 A1 | 3/2006 | Labrecque et al. | |
| 2006/0078586 A1 | 4/2006 | Ferraro et al. | |
| 2006/0112536 A1 | 6/2006 | Herweck | |

FOREIGN PATENT DOCUMENTS

| | | |
|---|---|---|
| EP | 1557183 A1 | 7/2005 |
| WO | WO-99/27989 | 6/1999 |
| WO | WO-00/12147 A1 | 3/2000 |
| WO | WO-00/40278 A1 | 7/2000 |
| WO | WO-01/15764 A1 | 3/2001 |
| WO | WO-01/24866 A1 | 4/2001 |
| WO | WO-02/22199 A2 | 3/2002 |
| WO | WO-02/076509 A2 | 10/2002 |
| WO | WO-03/028622 A2 | 4/2003 |
| WO | WO-03/039612 A1 | 5/2003 |
| WO | WO-2004/006976 A1 | 1/2004 |
| WO | WO-2004/028582 A1 | 4/2004 |
| WO | WO-2004/028610 A2 | 4/2004 |

OTHER PUBLICATIONS

International Search Report for Application No. PCT/US2006/038861, dated Mar. 5, 2007.

Clauβ, Wolfram, et al., "No Difference Among Modern Contrast Media's Effect on Neointimal Proliferation and Restenosis After Coronary Stenting in Pigs," *Investigative Radiology*, vol. 38(12):743-749 (2003).

Salu, K.J., et al., "Latrunculin A inhibits smooth muscle cell proliferation adn neointimal formation in a porcine coronary stent model," *European Heart Journal*, vol. 4:143 (2002).

Scheller, Bruno, et al., "Addition of Paclitaxel to Contrast Media Prevents Restenosis After Coronary Stent Implantation," *Journal of the American College of Cardiology*, vol. 42(8):1415-1420 (2003).

Scheller, Bruno, et al., "Paclitaxel Balloon Coating, a Novel Method for Prevention and Therapy of Restenosis," *Circulation*, vol. 110:810-814 (2004).

Scheller, B., et al., "Intracoronary paclitaxel added to contrast media inhibits in-stent restenosis of porcine coronary arteries,"*European Heart Journal*, vol. 4:188 (2002).

Scheller, B., et al., "Lack of cardiotoxicity after intracoronary paclitaxel application,"*European Heart Journal*, vol. 4:295 (2002).

Scheller, B., et al., "Short-term exposure of vascular smooth muscle cells (VSMC to a contrast medium-paclitaxel formulation inhibits proliferation in vitro,"*European Heart Journal*, vol. 4:536 (2002).

Scheller, Bruno, "Paccocath ISR I trial," Euro PCR05 presentation.

van der Giessen, Wim, "Glimpse into the future—Part II, Beyond the DES, A Nitric Oxide Eluting System," Euro PCR, presentation.

International Search Report Application No. PCT/US04/30173, dated Mar. 8, 2006.

U.S. Appl. No. 60/464,724 of the U.S. Pub. No. 2004/0230176.

* cited by examiner

METHOD OF COATING A FOLDED MEDICAL DEVICE

RELATED APPLICATIONS

This application claims priority to, and the benefit of, and is a continuation-in-part application of co-pending U.S. patent application Ser. No. 10/943,075, filed Sep. 15, 2004, which claims priority to U.S. Provisional Application No. 60/503,357, filed Sep. 15, 2003, for all subject matter common to said applications. The disclosures of all of the above-mentioned applications are hereby incorporated by reference herein in their entirety.

FIELD OF THE INVENTION

The present invention relates to a method of making a coated medical device, and more particularly to a method of coating a medical device in a collapsed, or partially collapsed and potentially folded configuration to control an amount of coating distribution to the medical device, and subsequent coating distribution to a targeted tissue location within a patient upon implantation.

BACKGROUND OF THE INVENTION

Mechanical drug and agent delivery devices are utilized in a wide range of applications including a number of biological applications, such as catheter interventions and other implantable devices used to create a therapeutic or other biological effect within the body. Often, such delivery devices take the form of radially expandable devices used to mechanically open an occluded or narrowed blood vessel. For example, inflatable non-elastomeric balloons have been utilized for treatment of body passages occluded by disease and for maintenance of the proper position of catheter-delivered medical devices, such as stents, within such body passages. With the use of drug carrying polymers applied to the stents to form drug eluting stents, such stents are placed within body lumens with drugs or agents embedded therein for release of the drug or agent within the body.

Some intervention balloon catheters are made to deliver a systemic bolus of liquid or gas that includes a drug, to a targeted tissue location within the body using an open catheter lumen or channel located at some length along the catheter shaft. Unfortunately, when such systemic delivery means are used to deliver a controlled volume of medication to a desired tissue location, a majority of the medication is lost to systemic circulation because of an inability of the drug to quickly penetrate local tissue. Generally, most liquid formulations containing a drug or agent that is delivered to the targeted tissue location by liquid bolus does not penetrate the tissue sufficiently at the targeted tissue location to result in a significant therapeutic effect, and is consequently washed away by body fluids. This systemic dilution substantially diminishes the effectiveness of the drugs or agents provided through such delivery devices, and increases the likelihood of a greater systemic effect caused by the large quantity of drug or agent washed into the bloodstream. To compensate for such delivery inefficiency, the dose of drugs or agents must be volumetrically increased in anticipation that they will be principally washed away before therapeutically effecting the localized or targeted tissue area. However, because of the risk of increased systemic effects and possibly toxic overload, the volume of the drugs or agents must not exceed that which can still be considered safe for exposure by systematic dilution and subsequent systematic distribution throughout the patient's body. The drug or agent used in such an intervention delivery method must be safe enough in its diluted state to be washed away to other parts of the patient's body and not have unwanted therapeutic or otherwise detrimental effects. There is a delicate balance between making the drugs or agents sufficiently concentrated to have therapeutic characteristics at the targeted tissue location, while also being sufficiently diluted to avoid harmful effects after being washed away into the body's systemic circulation.

Alternative to a systemic delivery, a local delivery of therapeutic agent can be administered. The local delivery can involve provision of a therapeutic agent using an applicator or as a portion of a coating on an implanted medical device. With provision of the drug or agent directly at the desired targeted tissue location, the systemic effects can be drastically reduced and the concentration of the drug or agent at the targeted tissue location can be substantially increased. One method for increasing the amount of drug at a targeted tissue location is to deliver the drug in relatively viscous configurations, such that when applied to the targeted tissue location, the drug or agent is not easily flushed away due to the adhesion of the viscous configuration to the tissue.

In accordance with certain configurations and embodiments for the local delivery of a therapeutic agent to a targeted tissue location, a balloon catheter can be utilized to transport a therapeutic agent, and then apply the therapeutic agent, to the targeted tissue location. However, in a collapsed or folded configuration, it can be difficult to evenly distribute the coating across the outer surface of the balloon, or provide a sufficient amount of coating on the exposed portions of the balloon surface. A more viscous coating can have a heavier drug load, but not evenly coat the collapsed or folded balloon, while a less viscous coating can penetrate into the folds of the collapsed or folded balloon, but may not have a high drug concentration.

SUMMARY

There is a need for a method of coating a medical device, such as a collapsed, wrapped, or folded catheter balloon, that can manipulate drug loading and coating viscosity to predictably result in a desired amount of therapeutic agent or agents applied to a medical device and correspondingly available for application to a targeted tissue location. The present invention addresses this need.

In accordance with one example embodiment of the present invention, a method of forming a coating on a medical device includes providing the medical device having a surface in a collapsed configuration with at least one fold. A coating material formulation is determined to achieve a predetermined coverage of the surface of the medical device and a predetermined thickness of the coating. The coating material is applied to form the coating on the medical device. The coating is compositioned to transfer and adhere to a targeted tissue location.

In accordance with aspects of the present invention, the medical device can be a balloon, more specifically a balloon catheter, or an angioplasty balloon.

In accordance with further aspects of the present invention, the step of determining the coating material formulation can include selecting between a relatively less viscous coating material for improved coverage of the medical device and a relatively more viscous coating material for a thicker coating on the medical device. The step of determining the coating material formulation can include selecting at least one therapeutic agent for incorporation into the coating material. The step of determining the coating material formulation can include mixing at least one therapeutic agent with a solvent as a portion of the coating material. The step of determining the coating material formulation can include selecting a non-polymeric bio-absorbable component to form a portion of the coating material. The step of determining the coating material formulation can include selecting a non-polymeric bio-absorbable cross-linked gel component to form a portion of the coating material.

In accordance with further aspects of the present invention, the step of determining the coating material formulation includes selecting between a relatively less viscous coating material between about 1 cPs and about 1,500 cPs for improved coverage of the medical device and a relatively more viscous coating material between about 10,000 cPs and about 100,000 cPs for a thicker coating on the medical device. The coating material formulation can have a viscosity of between about 1 cPs and about 100,000 cPs.

In accordance with further aspects of the present invention, the step of applying the coating material formulation can include removing solvent from the coating material prior to application to the medical device. Alternatively, the step of applying the coating material formulation can include removing solvent from the coating material subsequent to application to the medical device.

In accordance with one example embodiment of the present invention, a radially expandable medical device with a coating formed thereon includes a body having an interior and an exterior surface. A therapeutic coating is applied to at least a portion of the exterior surface of the body when in a collapsed configuration with at least one fold. The coating is compositioned to transfer and adhere to a targeted tissue location.

In accordance with aspects of the present invention, the coating material formulation can be a relatively less viscous coating material which substantially covers the surface of the medical device. Alternatively, the coating material formulation can be a relatively more viscous coating material which covers only a portion of the surface of the medical device. The coating material formulation can include at least one therapeutic agent. The coating material formulation can include at least one therapeutic agent mixed with a solvent. The coating material formulation can include a non-polymeric bio-absorbable component, such as a non-polymeric bio-absorbable cross-linked gel component.

In accordance with further aspects of the present invention determining the coating material formulation has a relatively less viscous coating material between about 1 cPs and about 1,500 cPs. Alternatively, the coating material formulation can have a relatively more viscous coating material between about 10,000 cPs and about 100,000 cPs. Furthermore, the coating material formulation can have a viscosity of between about 1 cPs and about 100,000 cPs.

In accordance with further aspects of the present invention, the coating material formulation is applied to the medical device subsequent to removal of solvent from the coating material. Alternatively, the coating material formulation includes a solvent subsequent to application to the medical device, wherein the solvent is removed prior to clinical.

BRIEF DESCRIPTION OF THE DRAWINGS

The present invention will become better understood with reference to the following description and accompanying drawings, wherein.

DETAILED DESCRIPTION

Figure 1A:
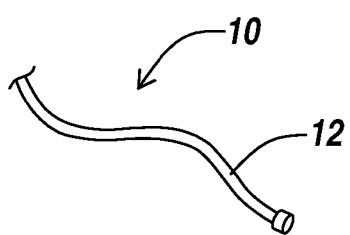
FIGS. 1A, 1B, 1C, 1D, 1E, 1F, and 1G are perspective illustrations of a variety of medical devices according to aspects of the present invention.
Figure 1B:
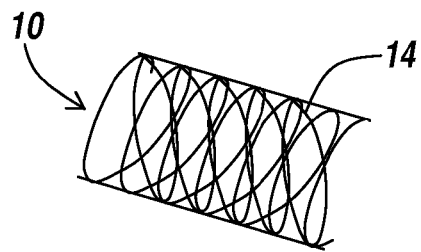
Figure 1C:
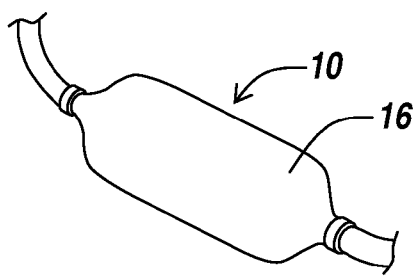
Figure 1D:
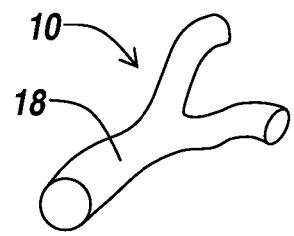
Figure 1E:
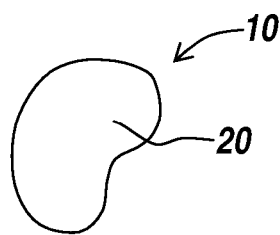
Figure 1F:
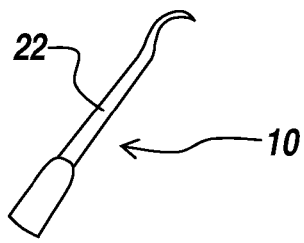
Figure 1G:

An illustrative embodiment of the present invention relates to use of a non-polymeric and/or biological coating that has been made to deliver a therapeutic agent or drug when applied to interventional medical devices for uniform drug distribution and cellular uptake by a targeted treatment area within the body. The present invention makes use of a sterile non-polymeric coating capable of being carried by a sterile medical device to a targeted tissue location within the body following radial expansion. The therapeutic coating transfers off the medical device without causing trauma to the local tissue being treated due in part to a biological attraction and in part to a physical transference from the medical device to the targeted tissue location in contact with the medical device. The present invention more particularly relates to a method of predictably coating the medical device in the example embodiment wherein the medical device is collapsed, wrapped, and/or folded, and is conventionally administered to a targeted tissue location within a patient in a collapsed, wrapped, and/or folded configuration, which may then be expanded for application of the coating to the tissue. The type of medical device to which the therapeutic substance is applied can vary, as can the method of substance transference of the non-polymeric coating from the medical device carrier and into the tissue of the body. In addition, the present invention has application in a number of different therapeutic blood vessel reperfusion techniques, including angioplasty, stent deployment, transcatheter balloon irrigation, angiography, embolic protection procedures, and catheter interventions.

FIGS. 1A through 7, wherein like parts are designated by like reference numerals throughout, illustrate example embodiments of an application of a therapeutic coating to a medical device for application to a targeted tissue location within a patient, according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed in a manner still in keeping with the spirit and scope of the present invention.

The phrase "therapeutic drug and/or agent", "therapeutic coating", and variations thereof, are utilized interchangeably herein to indicate single drug or multiple therapeutic drugs, single or multiple therapeutic agents, or any combination of single or multiple drugs, agents, or bioactive substances. Such drugs or agents include, but are not limited to, those listed in Table #3 below herein. As such, any subtle variations of the above phrase should not be interpreted to indicate a different meaning, or to refer to a different combination of drugs or agents. The present invention is directed toward improved transference delivery of therapeutic drugs and/or agents, or any combination thereof, as understood by one of ordinary skill in the art.

It has been found, surprisingly, that certain biological oils and fats with particular levels of viscosity temporarily adhere sufficiently strong enough to both a temporary and permanently placed intraluminal medical device so that most of the biological coating remains on the intraluminal device as it is inserted into an internal body cavity, passageway, or tissue space of a patient. Once the medical device is positioned within the body of the patient, the coating, with the therapeutic agents or ingredients contained thereto, can be transferred directly into the targeted tissue by the lypophilic absorptive action of the coating. The natural attraction and cellular uptake of the oil and fat by the tissue causes an unexpected benefit for efficient drug permeation and delivery of the targeted treatment area within the body. As with any localized drug delivery system, maximizing drug permeation to the tissue treatment area without incurring high dose systemic load to the outer surface of the cell membrane is considered the ideal method of choice. Use of a biological oil or fat that has been carefully mixed with a drug ingredient has been found to substantially improve the effective penetration of the drug ingredient into local tissue by bio-absorption of the oil drug complex. Because of the biological attraction of the oil and fat complex is high for many tissues within the body, the oil and fat complex readily transfers from the medical device chemically intact, without need for a secondary biochemical reaction or biological reaction to remove the oil and fat coating from the medical device. The therapeutic oil and fat complex readily transfers off the medical device when engaged tightly to a targeted tissue location with sufficient dwell time to allow the coated medical device to remain in close contact with the tissue for a short period of time. Once the coated device becomes adequately engaged with the targeted treatment zone, the oil and or fat complex readily transfers off during radial expansion of the medical device with the therapeutic ingredients intact, directly onto the contacted tissue with limited systemic effect.

It has further been found that certain oils and fats can permeate the tissue of a patient more rapidly than other materials can penetrate the tissue. More specifically, if a targeted tissue location within a body cavity requires the application of a therapeutic agent, the therapeutic agent can be applied to the targeted tissue location using a variety of different methods. The permeation of the tissue at the targeted tissue location by the therapeutic agent can be improved by mixing the therapeutic agent with a biological oil or fat, which permeates the tissue more efficiently than most therapeutic agents alone. When a therapeutic agent has been carefully solubilized, saturated, or mixed without polymerizing the agents into the oil or fat, such a therapeutic complex allows the medication to adequately permeate the tissue cause a therapeutic response to the tissue. By chemically stabilizing the active ingredients into the oil or fat without chemical polymerization of the oil, fat and or drug ingredient, the complex sufficiently delivers a dose of medication or drug directly into the tissue. Thus, a mixture of an oil or fat and a therapeutic agent, without any chemical bonds formed between the oil or fat and the therapeutic agent, allows a medication to be more efficiently delivered in a form suitable for permeation into the tissue when engaged within a patient than local medication delivery without the presence of a non-polymerized oil or fat complex.

Rather than reliance upon a chemical bond between drug ingredient and the carrier, selected biological fats and oils allow the therapeutic agents to solubilize, mix, or be carried intact within the oil or fat to form an atraumatic therapeutic delivery complex. The therapeutic agent can further be nano-particlized, dissolved, emulsified, or otherwise suspended within the oil or fat, enabling the therapeutic agents to be simultaneously absorbed by the tissue during the oil and fat absorption by the tissue.

It has been found experimentally that use of an oil or fat reduces the likelihood of there being an inflammatory reaction caused by the introduction of the therapeutic agent to the cells when exposed to the oil and fat complex. It is known that certain oils and fats, such as omega 3 fatty acids, are not only well received by body tissue, but have exhibited their own therapeutic and bioactive benefits. Such oils and fats reduce the otherwise common occurrence of an inflammatory reaction caused by the mechanical contact with the local tissue by the introduction of a mechanical delivery device, prosthesis, and/or therapeutic agent or medication. By mixing the therapeutic agent with the oil or fat, such inflammatory reactions are greatly reduced, thus improving the outcome of cellular uptake of a medication into the tissue and its biological effect. Furthermore, the oil or fat delivery system improves cellular uptake of the therapeutic agent during absorption of the smeared therapeutic coating.

Taking into account the ability of the oil or fat to perform as characterized above, the entire engagement area of targeted treatment zone can be treated. Example tissues can include a treatment zone within a blood vessel, a trachea, esophagus, urethra, or prostate lumen, and/or any engagement tissue location within the body. The localized treatment involves engaging a transferable biological oil or fat, combined with an active therapeutic agent or series of medications, including non-polymeric substances, which are engaged to a targeted treatment zone within the body by catheter intervention steps or device deployment methods used in radial expansion medical device intervention procedures.

In accordance with one example embodiment of the present invention, a medical device 10 is provided for application thereto of a therapeutic coating. The medical device can be any number of devices that have application within a patient. For example, as shown in FIGS. 1A through 1G, the medical device 10 can include a catheter 12 (such as a Foley catheter, suction catheter, urethral catheter, perfusion catheter, PTCA catheter, and the like), a stent 14, a radially expandable device 16 (such as a catheter balloon or a stent), a graft 18, a prosthesis 20, a surgical tool 22, a suture wire 24, or any other device or tool that makes contact with, or is proximal to, a targeted tissue location within a body cavity or body lumen.

For purposes of the remaining description, a particular embodiment of the present invention makes use of the radially expandable device 16 connected to the catheter 12, as utilized in conjunction with the stent 14, for an angioplasty type of procedure. However, it should be noted that the present invention is not limited to the particular system and method as described herein, but rather has application to a number of different medical devices 10 as identified above. It should furthermore be noted that the remaining description focuses on an angioplasty application of the above medical devices in combination with the therapeutic coating. One of ordinary skill in the art will appreciate that the present invention has application to medical devices in general having a collapsed, wrapped, and/or folded configuration that requires a coating be applied thereto. The radially expandable device 16 is merely one implementation of such a medical device.

Figure 2:
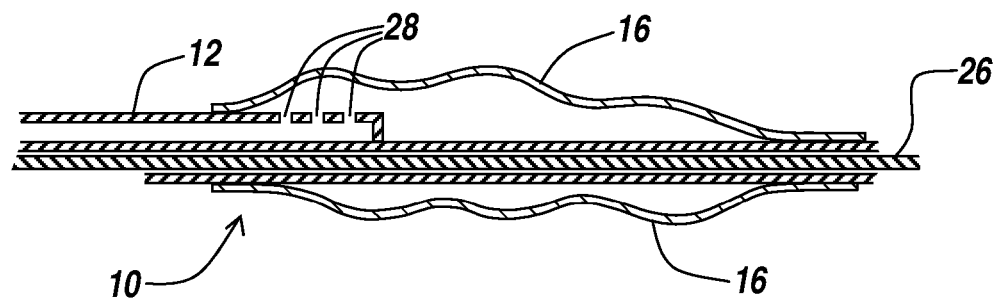
FIG. 2 is a diagrammatic cross-sectional view of a deflated radially expandable device, according to one aspect of the present invention.
Figure 3:
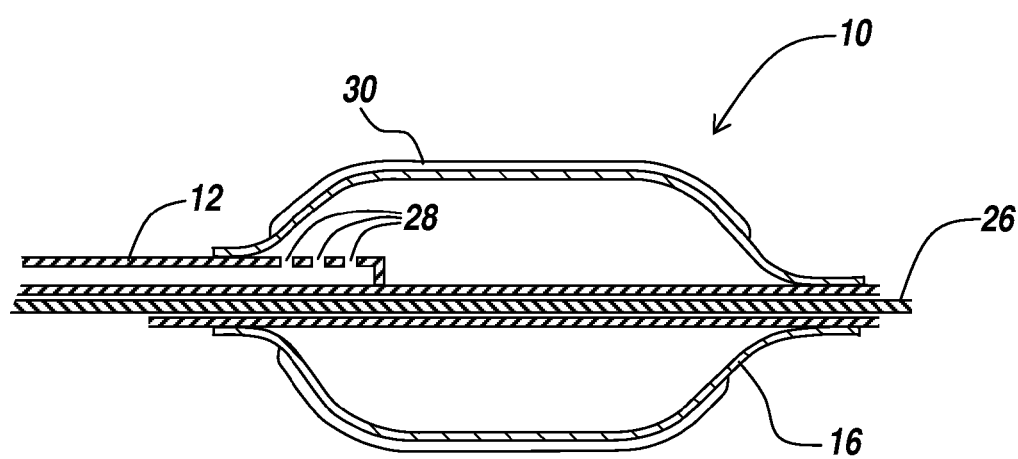
FIG. 3 is a diagrammatic cross-sectional view of the radially expandable device of FIG. 2 in expanded configuration, according to one aspect of the present invention.

In accordance with one example embodiment of the present invention, a radially expandable device 16 is constructed of a generally inelastic, polyester nylon blend material as illustrated in FIGS. 2 and 3. A catheter 12 and radially expandable device 16 are provided as shown in FIG. 2. The catheter 12 includes a guide wire 26 for guiding the catheter 12 and radially expandable device 16 to the body lumen. The catheter 12 has a number of openings 28 for providing a fluid to inflate the radially expandable device 16. FIG. 3 shows the radially expandable device 16 inflated.

Radially expandable devices in accordance with the present invention are suitable for a wide range of applications including, for example, a range of medical treatment applications within the body. Exemplary biological applications include use as a catheter balloon for treatment of implanted vascular grafts, stents, a permanent or temporary prosthesis, or other type of medical implant, used to treat a targeted tissue within the body, and treatment of any body cavity, space, or hollow organ passage(s) such as blood vessels, the urinary tract, the intestinal tract, nasal cavity, neural sheath, bone cavity, kidney ducts, and those previously intervened body spaces that have implanted vascular grafts, stents, prosthesis', or other type of medical implants. The catheter balloon can be of the type with a catheter passing through a full length of the balloon, or of the type with a balloon placed at an end of a catheter. Additional examples include as a device for the removal of obstructions such as emboli and thrombi from blood vessels, as a dilation device to restore patency to an occluded body passage as an occlusion device to selectively deliver a means to obstruct or fill a passage or space, and as a centering mechanism for transluminal instruments and catheters. The radially expandable device 16 can also be used as a sheath for covering conventional catheter balloons to control the expansion of the conventional balloon. Furthermore, the radially expandable device 16 can be porous or non-porous, depending on the particular application.

The body of the example radially expandable device 16 is deployable upon application of an expansion force from a first, reduced diameter configuration, illustrated in FIG. 2, to a second, increased diameter configuration, illustrated in FIG. 3. The body of the radially expandable device 16 preferably features a monolithic construction, i.e., a singular, unitary article of generally homogeneous material, however the monolithic construction is not required for implementation of the coating method of the present invention. The example radially expandable device 16 can be, for example, manufactured using an extrusion and expansion process. In addition, the radially expandable device 16 is merely one example embodiment. Any therapeutic drug or agent delivery device capable of sustaining a desired elevated pressure as described below, some of which can deliver a fluid with a therapeutic drug or agent under pressure to an isolated location, as understood by one of ordinary skill in the art, can be utilized, depending on the particular application. As shown, the radially expandable device 16 is an expandable shape that can be coupled with a catheter or other structure, potentially able to provide fluid (in the form of a slurry of nanoparticles, semi-solid, solid, gel, liquid or gas, if fluid delivery is desired and the device is porous) to the radially expandable device 16. If the radially expandable device 16 is not porous, then the catheter can deliver a fluid (of a number of different types) to inflate the radially expandable device 16 and maintain a desired pressure. The material utilized for the radially expandable device 16 can be, for example, PTFE or PET, among other materials known to those of ordinary skill in the art, depending on the particular application desired.

The radially expandable device 16 can be dependably and predictably expanded to the predefined, fixed maximum diameter and to the predefined shape independent of the expansion force used to expand the device.

The radially expandable device 16 can be generally tubular in shape when expanded, although other cross-sections, such as rectangular, oval, elliptical, or polygonal, can be utilized, depending on a particular application. The cross-section of the radially expandable device 16 can be continuous and uniform along the length of the body. However, in alternative embodiments, the cross-section can vary in size and/or shape along the length of the body. FIG. 2 illustrates the radially expandable device 16 relaxed in the first, reduced diameter configuration. The radially expandable device 16 has a central lumen extending along a longitudinal axis between two ends of the device.

A deployment mechanism in the form of an elongated hollow tube, such as the catheter 12, is shown positioned within the central lumen of the radially expandable device 16 to provide a radial deployment or expansion force to the radially expandable device 16. The radial deployment force effects radial expansion of the radially expandable device 16 from the first configuration to the second increased diameter configuration illustrated in FIG. 3. The radially expandable device 16 can be formed by thermal or adhesive bonding, or attached by other means suitable for inhibiting fluid leakage where unwanted.

The catheter 12 includes an internal, longitudinal extending lumen and a number of openings 28 that provide for fluid communication between the exterior of the catheter 12 and the lumen. The catheter 12 can be coupled to a fluid source or sources to selectively provide fluid to the radially expandable device 16 through the openings 28. The pressure from the fluid provides a radially expandable force on the body 12 to radially expand the body 12 to the second, increased diameter configuration. Because the body 12 is constructed from an inelastic material, uncoupling the tube 20 from the fluid source or otherwise substantially reducing the fluid pressure within the lumen 13 of the body 12, does not generally result in the body 12 returning to the first, reduced diameter configuration. However, the body 12 will collapse under its own weight to a reduced diameter. Application of negative pressure, from, for example, a vacuum source, can be used to completely deflate the body 12 to the initial reduced diameter configuration.

One skilled in the art will appreciate that the radially expandable device 16 is not limited to use with deployment mechanisms employing a fluid deployment force, such as the catheter 12. Other known deployment mechanisms can be used to radially deploy the radially expandable device 16 including, for example, mechanical operated expansion elements, such as mechanically activated members or mechanical elements constructed from temperature activated materials such as nitinol.

Various fluoropolymer materials are additionally suitable for use in the present invention. Suitable fluoropolymer materials include, for example, polytetrafluoroethylene ("PTFE") or copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. PTFE is utilized most often. Accordingly, while the radially expandable device 16 can be manufactured from various fluoropolymer materials, and the manufacturing methods of the present invention can utilize various fluoropolymer materials, the description set forth herein refers specifically to PTFE. In addition, PET or polyester nylon blend can be utilized, depending on the desired material properties.

Turning now to an example application of the radially expandable device 16, a description of an angioplasty will be described. In general, an angioplasty procedure is a procedure used to widen vessels narrowed by stenosis, restenosis, or occlusions. There are a number of different types of angioplasty procedures. In individuals with an occlusive vascular disease such as atherosclerosis, blood flow is impaired to an organ, such as the heart, or to a distal body part, such as an arm or leg, by the narrowing of the vessel's lumen due proliferation of a certain luminal cell type that has been impaired by vulnerable plaques, fatty deposits or calcium accumulation. The angioplasty procedure is a mechanical radial expansion procedure performed to radially open or widen the cross-sectional area of the vessel. Once the reperfusion procedure is completed, a desired blood flow returns within the mechanically opened area.

Over time, the vessel may constrict again, e.g., cellular proliferation called restenosis. The angioplasty procedure can be performed to re-open the vessel to a larger cross-sectional area. To prevent recoil or help control the occurrence or rate of restenosis, a stent can be implanted in the vessel. The stent is typically in the form of a radially expandable porous metal mesh tube, which following expansion forms a supporting scaffolding structure. As with any non-biological or foreign object or material in the body, like a stent or polymer coating, the risk of both acute and chronic inflammation and thrombosis is increased. Inflammation is due in part to the acute natural foreign body reaction. Inflammation caused by foreign body response is a primary reason why patients receive systemic medication, including, anti-inflammation, anti-proliferation, and anti-clotting medications before, during, and after interventional procedures, including stent implantations. However, such medications are not delivered specifically at the location of the injury to the vessel at the time of reperfusion injury or radial stent deployment into the vessel wall.

Generally, the implantation of a stent follows an angioplasty, but this is not always a requirement. For many patients, a direct stenting technique may be preferred to speed the reperfusion of the vessel, and to improve the delivery of the implant with a one step technique. In either instance, the stent is positioned in the vessel at the targeted tissue location by use of a deflated radially expandable balloon catheter. The radially expandable catheter device is inflated, expanding the stent against the vessel walls. The radially expandable catheter device is removed, leaving the stent in place in an expanded condition to mechanically hold the vessel open. Occasionally, another radially expandable balloon catheter device is inserted either entirely or partially into the previously stented vessel at the location of the stent and inflated to ensure the stent is properly expanded throughout so as to not migrate or move along the vessel wall, and to insure no gaps occur under the expanded stent, which are sources for excessive clot formation when not fully expanded.

In addition to the radially expandable device 16, FIG. 3 shows a therapeutic coating 30 applied to the radially expandable device 16. The therapeutic coating is applied to the medical device 10, in this case the radially expandable device 16, to create a therapeutic effect on the tissue at the targeted tissue location in a patient. The inclusion of the therapeutic coating 30 creates the opportunity to provide a medical or therapeutic effect for tissue that makes contact with the medical device 10. The therapeutic effect can be varied by the particular therapeutic agent incorporated into the therapeutic coating 30. The therapeutic coating 30 is made to coat the medical device 10 in a manner such that an efficacious amount of the therapeutic coating 30 does not wash away with bodily fluid passing by the medical device 10. The therapeutic coating 30 additionally will transfer from the medical device 10 to the targeted tissue location of the patient upon substantive contact between tissue and the medical device 10, and remain at or on the targeted tissue location to penetrate the tissue. The therapeutic coating can be applied to the radially expandable device 16, e.g., at a manufacturing stage, or just prior to insertion of the radially expandable device 16 into the body lumen.

As applied to the example angioplasty procedure, the present invention provides for an effective and efficient therapeutic agent or drug delivery, with more effective surface area coverage of the targeted tissue relative to known interventional drug eluting or systemic delivery procedures. The radially expandable devices expand from a first smaller diameter to a second larger diameter with a non-polymeric transferable therapeutic coating. Use of a therapeutic coating, agent, or biological material further aids in the transfer and tissue adhesion property of the material being applied directly onto and into the targeted treatment site during radial expansion of either the first intervention or second intervention, within or at least partially within the same targeted treatment sites.

The therapeutic coating 30 can be applied to the medical device 10 utilizing a number of different processes. In addition, the therapeutic coating can be sterilized prior to packaging, or prior to clinical use. The entire sterile medical device 10, or a portion thereof, can be submerged into a container containing the sterile therapeutic coating. The sterile medical device 10 can be rolled in a sterile tray containing the therapeutic coating. Additional methods of applying the therapeutic coating to the medical device can involve heating, or drying, or combinations thereof. One of ordinary skill in the art will appreciate that the invention is not limited by the particular method of preparing the sterile medical device 10 with the sterile therapeutic coating 30. Instead, any number of different methods can be utilized to result with the therapeutic coating 30 applied to the medical device 10 in a manner that promotes transfer of the therapeutic coating 30 to a targeted tissue location within a patient upon intervention by the medical device 10.

For example in accordance with the present invention, the therapeutic coating 30 can be applied with different relative viscosities, different drug (therapeutic agent) loadings, and applied to tightly wrapped or loosely wrapped radially expandable devices, all in different permutations, to result in the therapeutic coating 30 on the medical device 10.

The present invention can make use of a number of different therapeutic coatings 30 to coat the medical device 10. For purposes of illustration, a bio-absorbable cross-linked gel formulation. It should be noted that the term cross-linked gel, as utilized herein, refers to a gel that is non-polymeric and is derived from an oil composition comprising molecules covalently cross-linked into a three-dimensional network by one or more of ester, ether, peroxide, and carbon-carbon bonds in a substantially random configuration. In various exemplar embodiments, the oil composition comprises a fatty acid molecule, a glyceride, and combinations thereof.

The therapeutic coating 30 can provide a drug load or therapeutic agent load on the surface of the medical device 10. In the instance of the radially expandable device, such as a balloon attached to a catheter, the device can be placed at the targeted tissue location for delivery of the therapeutic agent via release off the coated balloon into the tissue. The efficiency of delivery is dependent upon the kinetics of transfer from the balloon into the targeted tissue location. The formulation of the therapeutic coating can be modified to impact the kinetics of transfer and as a result change the amount of drug or therapeutic agent uptake into the tissue.

Coating methodologies can initially involve the use of a solvent, which serves to dissolve or solvate the therapeutic agent into the coating formulation for subsequent application to medical devices. The solvent is completely removed prior to packaging the final coated product. The solvent can be removed from the coating material either before or after application of the coating material to the medical device. If the solvent is removed prior to coating the medical device, a relatively thicker therapeutic coating 30 results. A thicker and more viscous therapeutic coating 30 on the medical device 10 subsequently provides a relatively slower transference from the medical device to the targeted tissue location. Alternatively, coating methodologies that include leaving the solvent in the coating material for application to the medical device can be performed. If the solvent remains in the coating material and when first applied as the therapeutic coating 30, a relatively thinner and less viscous therapeutic coating 30 results. A thinner and less viscous therapeutic coating 30 on the medical device 10 subsequently provides a relatively faster transference from the medical device to the targeted tissue location.

As used herein, the term "viscosity" refers to the resistance of a fluid to shear or flow, and is a measure of the fluids adhesive/cohesive or frictional properties. This resistance is caused by intermolecular friction exerted when layers of fluids attempts to slide by an other. One of ordinary skill in the art would be readily able to measure the viscosity of the coating formulation by using, for example, a viscometer. The phrases "high viscosity" or "higher viscosity" refer to an increase in the resistance of a fluid to shear or flow, as compared to a reference fluid of "low viscosity" or "lower viscosity". The reference fluid, for purposes of this description, is intended as a fluid of similar viscosity to an oil-based material, such as fish oil, that has not been modified with additives, drugs, thickeners, or cured to any substantial degree to form or increase amounts of cross-links within the oil.

The units of viscosity can be centipoises (cP), centistokes (cSt), Saybolt Universal Seconds (SSU), Pascal seconds (Pa-s) and degrees Engler. In one embodiment, the oil-based reference fluid has a viscosity measurement from about 15 cPs to about 100,000 cPs. Accordingly, the low viscosity, or lower viscosity, coating formulation can have a viscosity of about 1 cPs (similar viscosity to that of water), of about 15 cPs (similar viscosity to that of glycol), of about 28 cPs (similar viscosity to that of linseed oil), of about 90 cPs (similar viscosity to that of olive oil), of about 180 cPs (similar viscosity to that of motor oil), of about 700 cPs (similar viscosity to that of heavy machine oil), of about 1,000 cPs (similar viscosity to that of SAE 50 motor oil), of about 1,500 cPs (similar viscosity to that of glycerin at 20° F.), or an amount generally proximal to, or equivalent to, such viscosity measurements. Likewise, the high viscosity, or higher viscosity, coating formulation can have a viscosity of about 10,000 cPs (similar viscosity to that of molasses), of about 20,000 cPs (similar viscosity to that of chocolate syrup), of about 28,000 cPs, of about 50,000 cPs (similar viscosity to that of ketchup), of about 100,000 cPs (similar viscosity to that of ketchup at 25° C.), or an amount generally proximal to, or equivalent to, such viscosity measurements. It should be noted that the present invention is by no means limited to the specific viscosity ranges described herein. One of ordinary skill in the art will appreciate that the present invention is directed to a method that takes into consideration relative viscosities of coating formulations and their corresponding ability to coat a medical device with varying degrees of surface coverage. The above viscosity measurements are intended to provide some general indication of the type of viscosities that can be utilized to form the coating formulations, and subsequent coatings. However, any coating formulation that can be applied to a medical device, including coating formulations that fall outside of the example ranges, fall within the scope of the present invention in that determinations of relative viscosities of the coating formulations are utilized in creating the coated medical device.

Figure 4:
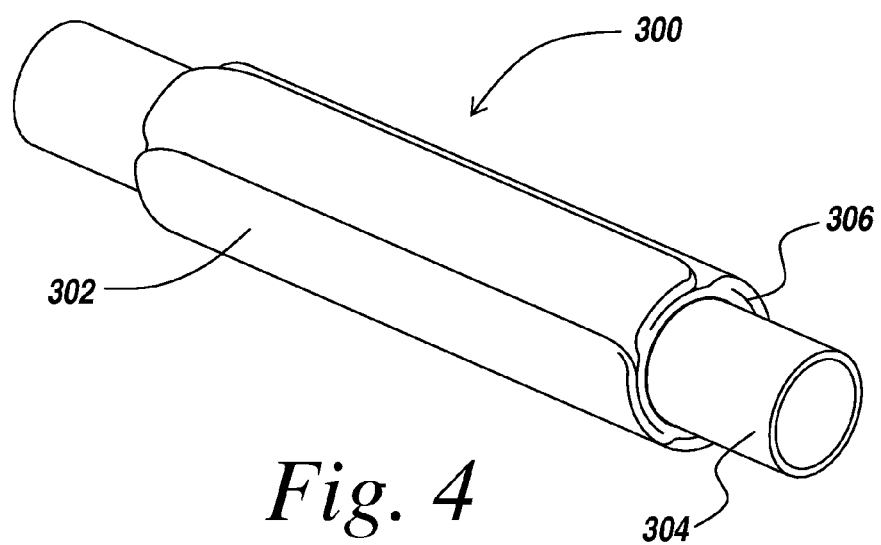
FIG. 4 is a diagrammatic illustration of a tightly wrapped radially expandable device, according to one aspect of the present invention.
Figure 5:
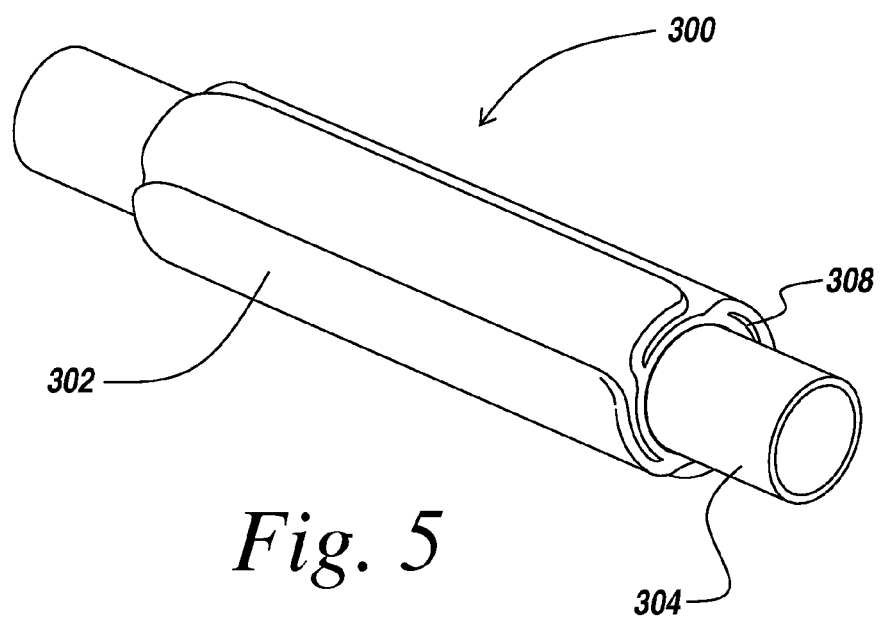
FIG. 5 is a diagrammatic illustration of a loosely wrapped radially expandable device, according to one aspect of the present invention.

One additional, but related, factor that influences the ability of the coating material to coat the medical device 10 to form the therapeutic coating 30, especially in the instance of the radially expandable device 16, or a balloon catheter device, is the degree to which the device is tightly folded or collapsed against itself. FIG. 4 shows a catheter balloon 300, such as an angioplasty type balloon, that is tightly wrapped as is commonly provided by catheter balloon manufacturers. The catheter balloon 300 includes the catheter 304 portion and the balloon 302 portion. The balloon 302 can be of the type used in conjunction with stents, or with a stent crimped thereon, as understood by one of ordinary skill in the art. The balloon 302 is tightly wrapped upon itself and the catheter 304, as evidenced by the minimal clearance 306 between flaps or folds of the balloon 302. In contrast, FIG. 5 shows the same catheter balloon 300 that has been unwrapped and more loosely re-wrapped together. The catheter balloon 300 includes the catheter 304 portion and the balloon 302 portion. The balloon 302 is more loosely wrapped upon itself and the catheter 304, as evidenced by the relatively greater clearances 308 between flaps or folds of the balloon 302 as compared with the catheter balloon 300 as illustrated in FIG. 4. Said differently, and with reference to Table #1 below, the tightly wrapped configuration, in accordance with one example embodiment of the present invention, has a measured outer diameter of about 0.037 inches. When the tightly wrapped configuration is unwrapped and then re-wrapped in a more loosely wrapped configuration, the measured outer diameter is on the order of about 0.041 inches.

Accordingly, as utilized herein, the terms "tightly wrapped" and "loosely wrapped" are intended as being relative to one another. The relative difference between a tightly wrapped balloon and a loosely wrapped balloon is evidenced by the example embodiment, and characterized by an example outer diameter measurement difference of about 0.004 inches on a 0.037 inch outer diameter tightly wrapped balloon (or about a 10% increase in the outer diameter). The example 10% increase is embodied in the increase in dimension of the greater clearance 308 relative to the minimal clearance 306. One of ordinary skill in the art will appreciate that the present invention is not limited to the specific diameter measurements described herein, or the relative percentage change in diameter measurements as an expression of tightly wrapped versus loosely wrapped. Rather, the example diameter measurements are merely intended to provide additional detail with regard to approximate scale of the relative relationship between a tightly wrapped balloon versus a loosely wrapped balloon.

For manufacturing, it is desirable to be able to load the therapeutic coating 30 onto the medical device 10 (for example, the catheter balloon 300) either tightly wrapped as shown in FIG. 4, or loosely wrapped as shown in FIG. 5, instead of requiring the balloon 302 be inflated for application of the coating. As understood by one of ordinary skill in the art, a fewer number of steps involved in manufacturing processes results in a more efficient manufacturing process.

In accordance with the present invention, methods are provided for coating the catheter balloon 300 (or other medical device) in one of the two folded configurations, without requiring partial or complete inflation of the balloon for application of the coating. A relatively less viscous coating material formulation in accordance with the present invention is more effective at completely covering and coating the surface of the balloon 302 that is tightly wrapped with minimal clearances 306 relative to a coating material of greater viscosity, because the coating material can gain better access to all of the folded surfaces through the minimal clearances 306. A more viscous, coating formulation does not achieve good access to all of the folded surfaces through the minimal clearances 306. However, the more viscous coating formulation results in a thicker therapeutic coating 30, and therefore a greater quantity of coating material per area covered, and a greater overall therapeutic agent or drug loading. The balloon 302 itself can be modified by being unfolded and re-folded in a looser manner, creating the greater clearances 308 between flaps or folds. In such a configuration, a less viscous coating material can again gain access to all of the folded surfaces through the greater clearances 308. In addition, the more viscous coating formulation can also gain better access to the folded surfaces through the greater clearances 308 relative to the access through the minimal clearances 306 of the tightly wrapped configuration. Variations in drug or therapeutic agent loading, coating material viscosity, and tightness of wrapping can influence the eventual coverage of the coating and thickness of the coating, and therefore the overall amount of coating and therapeutic agent or drug loaded on the balloon 302.

Figure 6:
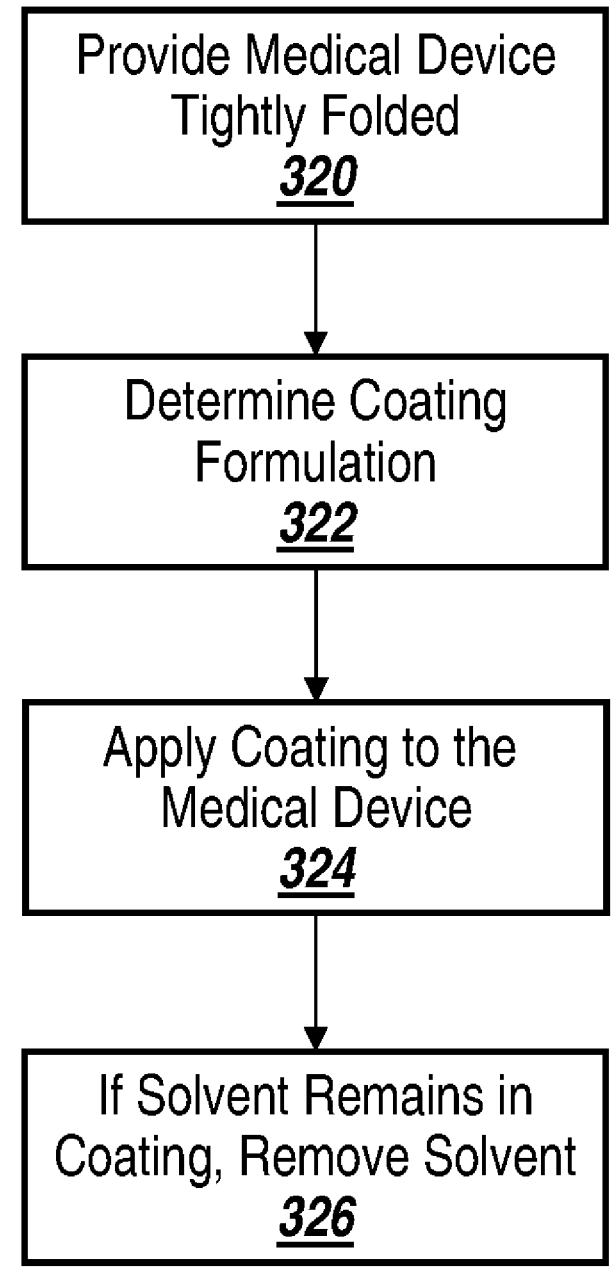
FIG. 6 is a flowchart showing a method of applying a coating to the device of FIG. 4, according to one aspect of the present invention.

FIG. 6 is a flowchart illustrating one method of coating a medical device, such as a balloon 302 of a balloon catheter 300, in accordance with the present invention. The catheter balloon is provided (step 320). In a first embodiment, the catheter balloon 302 is tightly wrapped, as conventionally provided by manufacturers and similar to the embodiment of FIG. 4. A determination is made as to what formulation of coating material to apply (relatively low viscosity or relatively high viscosity) considering such factors as degree of coverage desired on the balloon surface, total amount of coating material desired on the balloon, thickness of resulting coating desired, amount of drug or therapeutic agent loading on the balloon and in the coating, and the like (step 322). The coating material is applied to the medical device (step 324) to result in the therapeutic coating. If there is any solvent remaining in the coating, the solvent is removed, such as by vacuum or heat (step 326).

Figure 7:
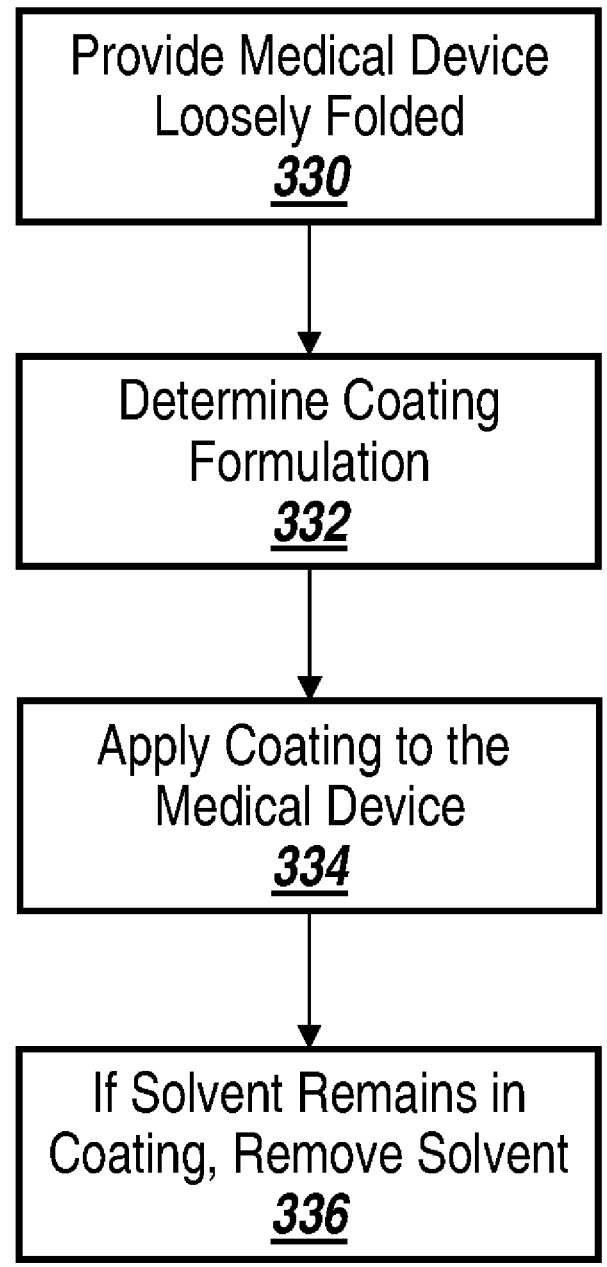
FIG. 7 is a flowchart showing a method of applying a coating to the device of FIG. 5, according to one aspect of the present invention.

FIG. 7 is a flowchart illustrating one method of coating a medical device, such as a balloon 302 of a balloon catheter 300, in accordance with the present invention. The catheter balloon is provided (step 330). In a second embodiment, the catheter balloon 302 is loosely wrapped, similar to the embodiment of FIG. 5. A determination is made as to what formulation of coating material to apply (lower viscosity formulation or higher viscosity formulation) considering such factors as degree of coverage desired on the balloon surface, total amount of coating material desired on the balloon, thickness of resulting coating desired, amount of drug or therapeutic agent loading on the balloon and in the coating, and the like (step 332). The coating material is applied to the medical device (step 334) to result in the therapeutic coating. If there is any solvent remaining in the coating, the solvent is removed, such as by vacuum or heat (step 336).

To demonstrate the application of the methods of the present invention, several example implementations were performed using rapamycin as the drug or therapeutic agent loaded into a coating carrier component of vitamin E and fish oil. Both relatively higher viscosity and relatively lower viscosity implementations were performed to highlight the ability to control the coating parameters as described herein.

Specifically, viscosity variations of the same coating materials were utilized in the example implementations. Rapamycin was mixed together with a mixture of 70% vitamin E and 30% Epax 3000TG Fish oil. The rapamycin, dissolved in nMp solvent, was mixed together with the vitamin E/fish oil mixture at a ratio of 50:50. Once the solvent was removed, the final drug concentration in the therapeutic coating was about 32%.

As described previously, the difference between a relatively higher viscosity coating formulation and a relatively lower viscosity coating formulation relates to when the solvent is removed in the process. For the low viscosity formulation, the nMp was removed after coating the balloon. For the high viscosity formulation, the nMp was removed prior to coating the balloon. The coating was applied to 4.0 mm×10 mm balloons. Table #1, below, illustrates the amount of drug (rapamycin) loaded onto the ballons using both the low viscosity and high viscosity coating formulations.

TABLE #1

| Wrapping Configuration | Low Viscosity Coating Formulation | High Viscosity Coating Formulation | Normalized using drug/mm$^2$ Low visc./ High visc. |
|---|---|---|---|
| Pre-Wrapped (a 0.037" profile) | 723 μg of drug | 980 μg of drug | 4.7/6.4 |
| Loosely Wrapped (to a 0.041" profile) | 949 μg of drug | 1095 μg of drug | 6.2/7.1 |

After demonstrating the results of the above Table #1, a further illustrative implementation demonstrated the ability of the drug to transfer from the coated balloon catheter using the same formulations implanted in pig vessels.

Specifically, 3.0 mm×10 mm balloons were coated with the low viscosity and high viscosity formulations of Table #1, prepared with two drug variations, namely, with rapamycin and with paclitaxel. The balloons were expanded in pig carotid arteries for 60 seconds. The vessels were then attached to a flow system and flushed with 1 liter of Krebs-Henseleit buffer to remove any loose coating. Fresh buffer solution was then re-circulated through the vessels for one hour at physiologically normal temperature and pressure. The vessels were then removed from the system and drug uptake into the tissue was determined using HPLC analysis. Table #2, below, shows the average uptake into the vessel segments for each drug type and low viscosity or high viscosity coating formulation.

TABLE #2

| Coating Formulation | Rapamycin | Paclitaxel |
|---|---|---|
| Low Viscosity Formulation | 3.26 μg/segment | 4.26 μg/segment |
| High Viscosity Formulation | 1.76 μg/segment | 3.48 μg/segment |

As evidenced in the described illustrative implementations, the efficiency of drug transfer into the tissue can be varied according to the coating process. Despite the ability to provide a thicker coating using the higher viscosity formulation, the lower viscosity formulation can be formulated to provide a higher drug uptake into the tissue. The interplay of each of the above-mentioned variables results in the desired drug loading and ultimately in the amount of drug uptake into the tissue. A thin coating carries less drug quantity, but has better coverage of the balloon surface, relative to the thick coating on a tightly folded or loosely folded balloon. The thick coating carries a higher drug loading, but has a lesser amount of coverage of the balloon surface when applied to a tightly folded balloon. However, as the above results illustrate, the lower drug loading in the thin coating can actually result in a higher drug uptake by the tissue, which is in part due to the improved surface coverage of the balloon by the coating.

The therapeutic coating 30 can be formed of a number of different agents and compositions. The therapeutic coating can be a non-polymeric, biologically compatible coating. The coating can be formed entirely of a single substance, or can be formed using a mixture, aggregate, compilation, composition, and the like, of two or more substances, including one or more different therapeutic agent nano-particles, one or more of which can be a therapeutic agent having therapeutic properties, and/or biological effects to the targeted tissue location.

In accordance with one example embodiment, the therapeutic coating can be formed of a non-polymeric, biologically compatible, oil or fat, such as the non-polymeric bio-absorbable cross-linked gel derived at least in part from a fatty acid. There are a number of different therapeutic agents that are either lipophilic, or do not have a substantial aversion to oils or fats. Such therapeutic agents can be mixed with the oil or fat, without forming a chemical bond, and delivered to a targeted tissue location within a patient in accordance with the teachings of the present invention. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs, and any additional desired therapeutic agents such as those listed in Table #3 below.

TABLE #3

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC |

TABLE #3-continued

| CLASS | EXAMPLES |
| --- | --- |
| | antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/ Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200, 985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

The act of mixing the therapeutic agent with the oil or fat results in a therapeutic mixture for application to the medical device 10 as a therapeutic coating. The therapeutic mixture can stick sufficiently well enough to the medical device, such as a delivery device or prosthesis, to transfer the therapeutic coating to a targeted tissue location within a patient following radial expansion of the device. An improved permeability of the tissue at the targeted tissue location by the oil or fat results in improved permeation by the therapeutic agent as well. In addition, a natural lipophilic tissue adherence characteristic of the oil or fat reduces the likelihood that most of the therapeutic mixture will be washed away by passing body fluids following placement of the device at the targeted tissue location. Therefore, the therapeutic mixture is held in place along the treatment area of the targeted tissue location, improving the permeation potential of the tissue by the mixture, and thus improving the therapeutic effect to the targeted treatment area within the body.

There are several oils and fats that are appropriate for use with the present invention. One fatty acid found to perform well was an omega 3 fatty acid, such as fish oil. Another component of the oils and fats found to function well with the present invention is alfa-tocopherol. There are a plurality of additional oils and fats and other components, some of which are listed in Table #4 below.

TABLE #4

Fish Oil
Cod-liver Oil
Squid Oil
Olive Oil
Linseed Oil
Sunflower Oil
Corn Oil
Palm/Palmnut Oil
Flax Seed Oil In addition, and as previously mentioned, the mixture of therapeutic agent and oil or fat can include other components such as a solvent. The solvent serves to control or adjust the viscosity of the mixture. Other components can be added to stabilize the therapeutic mixture or affect other characteristics of the mixture. Furthermore, the mixture itself can be modified, such as through hydrogenation.

The present invention relates to a plurality of combinations involving some form of therapeutic application of a therapeutic coating onto and into the targeted tissue location during use of a medical device supporting the therapeutic coating. Such combinations can include implantation procedures, such as a radial stent deployment procedure, to the same area location (within or partially within the same treatment location). The technique and device technology allows a multiple application step means to deliver more coating, medicated or therapeutic agent, or biological, over a larger surface area than can be applied solely by a single catheter step means, or by a single step means using solely a drug eluting stent means. Typically, a drug eluting stent has a surface area equal to no more than 20% of the vessel wall, and therefore cannot deliver a coating, medicated agent, or biological to more than 20% of the targeted tissue site. The method of the present invention provides a means to deliver more therapeutics over a larger treatment area. In addition, the use of the porous radially expandable device enables additional control over the amount of therapeutic coating delivered to the targeted tissue location, increasing the therapeutic effect of the coating.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the disclosed invention is reserved.

What is claimed is:

1. A radially expandable medical device with a coating formed thereon, comprising:
   a body having an interior and an exterior surface; and
   a coating material applied to at least a portion of the exterior surface of the body when in a collapsed configuration with at least one fold to form a therapeutic coating;
   wherein the coating is compositioned to transfer and adhere to a targeted tissue location; and
   wherein the coating material comprises a non-polymeric bio-absorbable cross-linked gel component.

2. The device of claim 1, wherein the medical device comprises a balloon.

3. The device of claim 1, wherein the medical device comprises a balloon catheter or an angioplasty balloon.

4. The device of claim 1, wherein the coating material is a viscous coating material which substantially covers the surface of the medical device.

5. The device of claim 1, wherein the coating material is a viscous coating material which covers only a portion of the surface of the medical device.

6. The device of claim 1, wherein the coating material has a viscosity between about 1 cPs and about 1,500 cPs.

7. The device of claim 1, wherein the coating material has a viscosity between about 10,000 cPs and about 100,000 cPs.

8. The device of claim 1, wherein the coating material has a viscosity of between about 1 cPs and about 100,000 cPs.

9. The device of claim 1, wherein the coating material further comprises at least one therapeutic agent.

10. The device of claim 1, wherein the coating material further comprises at least one therapeutic agent mixed with a solvent.

11. The device of claim 1, wherein the coating is applied to the medical device subsequent to removal of solvent from the coating material.

12. The device of claim 1, wherein the coating material further comprises a solvent subsequent to application to the medical device, wherein the solvent is removed prior to clinical use.

13. The device of claim 1, wherein the non-polymeric bio-absorbable component is derived from an oil composition.

14. The device of claim 13, wherein the oil composition comprises a fatty acid molecule or a glyceride.

* * * * *